United States Patent [19]

Raines

[11] Patent Number: 5,328,474
[45] Date of Patent: Jul. 12, 1994

[54] TAMPER RESISTANT SYRINGE CAP

[75] Inventor: Kenneth Raines, Bethlehem, Pa.

[73] Assignee: B. Braun Medical Inc., Bethlehem, Pa.

[21] Appl. No.: 118,682

[22] Filed: Sep. 10, 1993

Related U.S. Application Data

[63] Continuation of Ser. No. 867,458, Apr. 13, 1992, abandoned.

[51] Int. Cl.$^5$ .............. A61M 5/00; A61M 5/32; A61B 19/00; B65D 55/02
[52] U.S. Cl. .............. 604/110; 604/111; 604/192; 604/263; 604/404; 215/213; 215/250; 215/295; 215/302
[58] Field of Search .............. 128/917, 919; 206/364, 206/365; 215/201–202, 211–212, 213, 224, 249–253, 295, 302, 317, 318, 324, 334, 336–337; 220/214, 256–258; 604/110–111, 192, 263, 404

[56] References Cited

U.S. PATENT DOCUMENTS

| | | | |
|---|---|---|---|
| 749,422 | 1/1904 | Chapman | 215/250 |
| 752,250 | 2/1904 | Chapman | 215/250 |
| 1,153,236 | 9/1915 | MacIndoe | 215/213 |
| 3,469,726 | 9/1969 | Slack et al. | 215/213 |
| 3,811,590 | 5/1974 | Hall, Jr. | 215/302 |
| 4,273,248 | 6/1981 | Lehman | 215/334 |
| 4,571,242 | 2/1986 | Klein et al. | |
| 4,667,837 | 5/1987 | Vitello et al. | |
| 4,763,802 | 8/1988 | Johnston | |
| 4,840,619 | 6/1989 | Hughes | |
| 4,874,101 | 10/1989 | Zalut | |
| 4,899,897 | 2/1990 | Buttiker et al. | |
| 4,998,632 | 3/1991 | Morris, Sr. | 215/201 |
| 5,069,225 | 12/1991 | Okamura | |
| 5,114,029 | 5/1992 | Gibilisco | 215/334 |

Primary Examiner—Randall L. Green
Assistant Examiner—P. Zuttarelli
Attorney, Agent, or Firm—Shoemaker and Mattare, Ltd.

[57] ABSTRACT

A tamper-resistant closure for a medical injection device such as a syringe includes a cap having both a blind bore sized to receive and seat tightly against the syringe tip, to prevent material from entering or being withdrawn from the device. The cap has a threaded connection to the syringe tip, and is entirely covered by a loose-fitting shield having a one-way drive mechanism which prevents the cap from being unscrewed from the device while the shield is in place. The shield has at least one internal, frangible tang protruding obliquely into the envelope of the cap, so that the shield and cap can be easily assembled, but cannot thereafter be disassembled without breaking the tang and thus providing an indication of tampering.

13 Claims, 4 Drawing Sheets

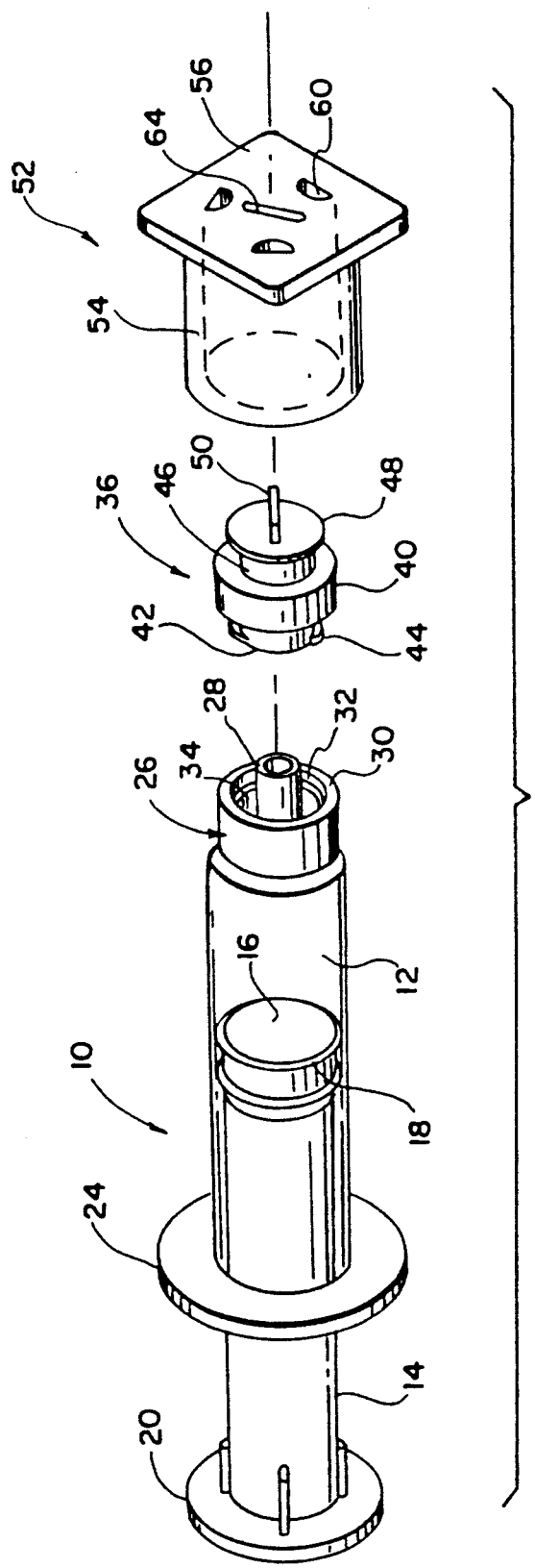

TAMPER RESISTANT SYRINGE CAP

This application is a continuation of application Ser. No. 07/867,458, filed Apr. 13, 1992, now abandoned.

BACKGROUND OF THE INVENTION

This invention relates to medical equipment, and particularly to a closure for preventing tampering with a filled syringe or the like.

In a hospital, after a pharmacist has filled a syringe with a medication, the syringe is then carried to the patient. Particularly when the contents of the syringe are a narcotic such as morphine, there is a risk that the person in custody of the syringe during transportation may withdraw its contents for his or her own purposes, perhaps then refilling the syringe with another liquid such as saline, and recapping the syringe to escape detection.

SUMMARY OF THE INVENTION

This invention is intended to prevent or at least impede tampering during transportation, and provides a readily noticeable indication of tampering. More generally, an object of the invention is to prevent contamination of syringes and their contents, by barring access to their outlet ports.

Another object of the invention is to enable one to screw a sealing cap onto the end of a syringe or the like, yet to prevent the cap from being unscrewed surreptitiously.

A related object is to simplify the manufacture, and reduce the costs, of a tamper-evident syringe cap.

These and other objects are attained by a tamper-resistant closure for a medical injection device such as a syringe, the closure including a cap having both a blind bore sized to receive and seat tightly against the syringe tip, to prevent material from entering or being withdrawn from the device. The cap has a threaded connection to the syringe tip, and is entirely covered by a loose-fitting shield having a one-way drive mechanism which prevents the cap from being unscrewed from the injection device while the shield is in place. The shield has at least one internal, frangible tang protruding obliquely into the envelope of the cap, so that the shield and cap can be easily assembled, but cannot thereafter be disassembled without breaking the tang and thus providing an indication of tampering.

BRIEF DESCRIPTION OF THE DRAWINGS

In the accompanying drawings,

FIG. 1 is an exploded isometric view of a syringe, and of a closure for the syringe embodying the invention;

DESCRIPTION OF THE PREFERRED EMBODIMENT

Figure 3:
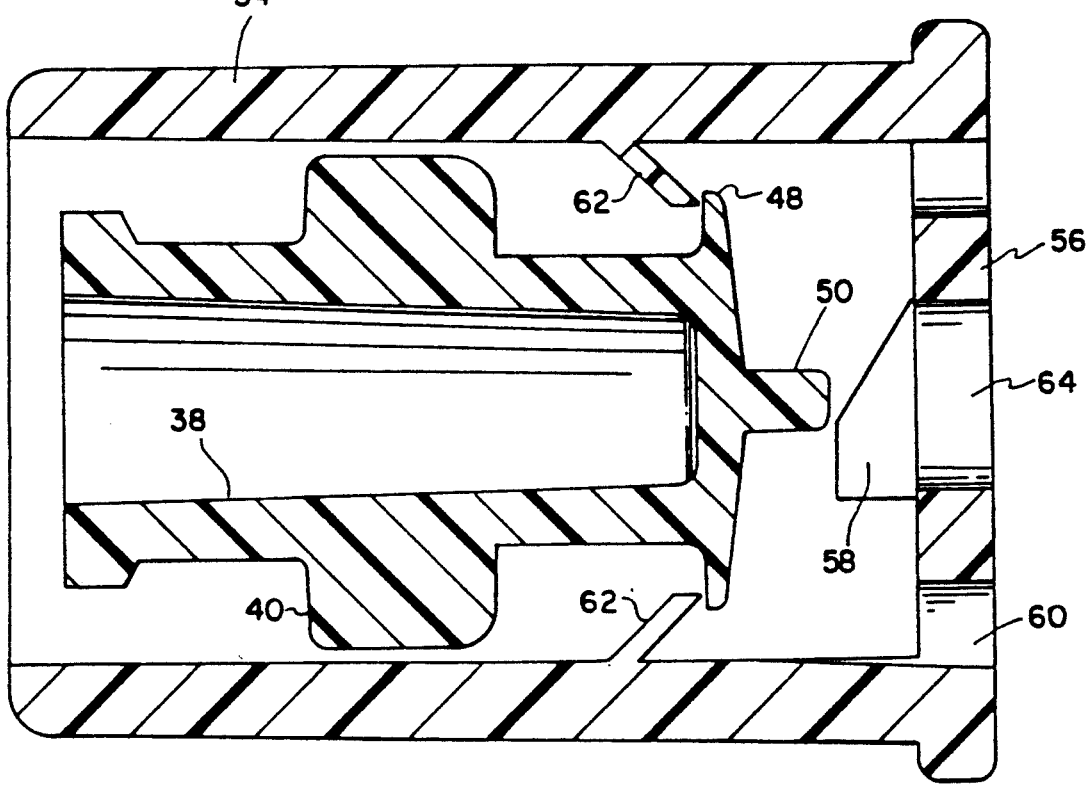
FIG. 3 is a sectional view, taken along the axial plane 3—3 in FIG. 2, showing both the shield, and the cap in its installed position.

The invention is embodied in an assembly comprising a syringe 10 including a barrel 12 and a plunger 14 telescopically received therein. A resilient piston 16 affixed at the distal end of the plunger has at least one sealing lip 18 (two are preferred) slightly compressed by the barrel, to prevent leakage around the piston. The proximal end of the plunger has and enlarged head 20 for engaging the thumb. A skirt or flange 24 at the proximal end of the barrel provides a finger hold.

A female lock 26 is provided around the slightly tapered tip 28 of the syringe. It may be molded with the syringe, and formed separately and then affixed to the syringe by ultrasonic welding or other secure methods. The luer lock comprises a tubular skirt 30 having internal, double-lead, right-hand helical threads 32 whose internal diameter substantially exceeds the outside diameter of the tip, so that an annular volume 34 is left between the threads and the tip.

Figure 5:
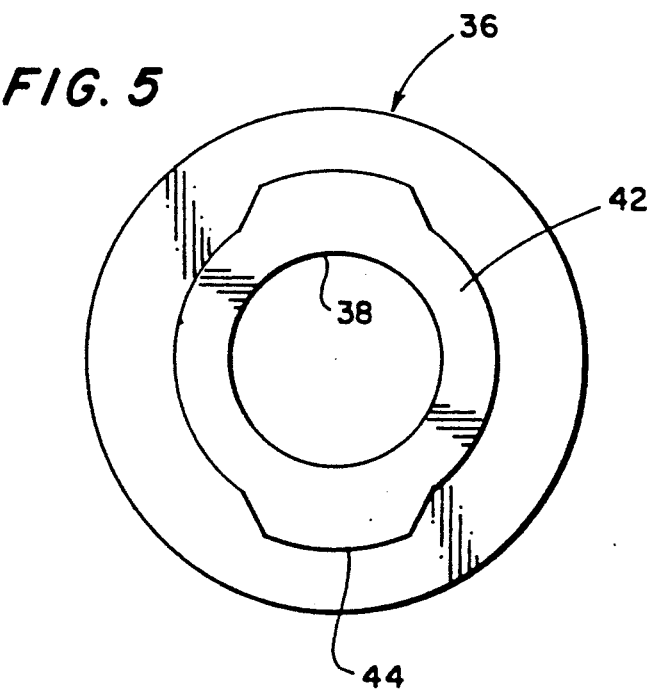
FIG. 5 is an end view of the cap, viewed in the direction of FIG. 2.

To prevent contamination of the syringe interior, via the nozzle, a cap 36 is provided. The cap has a central blind bore 38 (FIGS. 3 and 5) of uniform diameter which fits over the nozzle, seating tightly against it when the nozzle is inserted sufficiently far into the bore, short of the bottom of the bore. A enlarged collar 40 extends around the center of the cap. The proximal end 42 of the cap has a reduced diameter, and two lugs 44 extend from opposite sides of the proximal end. These lugs are sized to engage the internal threads on the luer lock, serving as male threads.

The distal end 46 of the cap also has a reduced diameter, except for a thin peripheral flange 48 having a diameter slightly less than that of the collar. The distal end terminals at a short, flat blade 50 arranged along a diameter of the cap.

To prevent people from unscrewing the cap, a shield 52 is installed over it. The shield has a tubular shell 54 slightly larger, in length and diameter, than the cap, so that the whole cap can fit loosely within the shield. The proximal end of the shield is open, while the distal end is closed by a square plate 56 perpendicular to the axis of the shell, and formed integrally with it.

Figure 2:
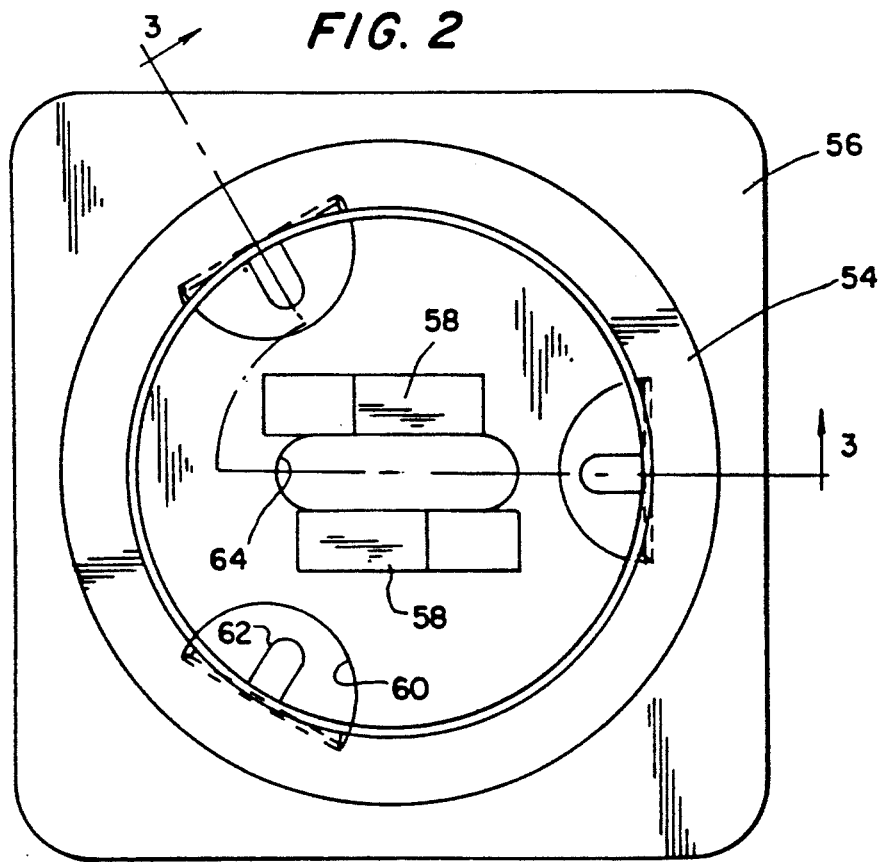
FIG. 2 is an end view, taken in the direction 2—2 in FIG. 1, of the shield portion of the invention.
Figure 4:
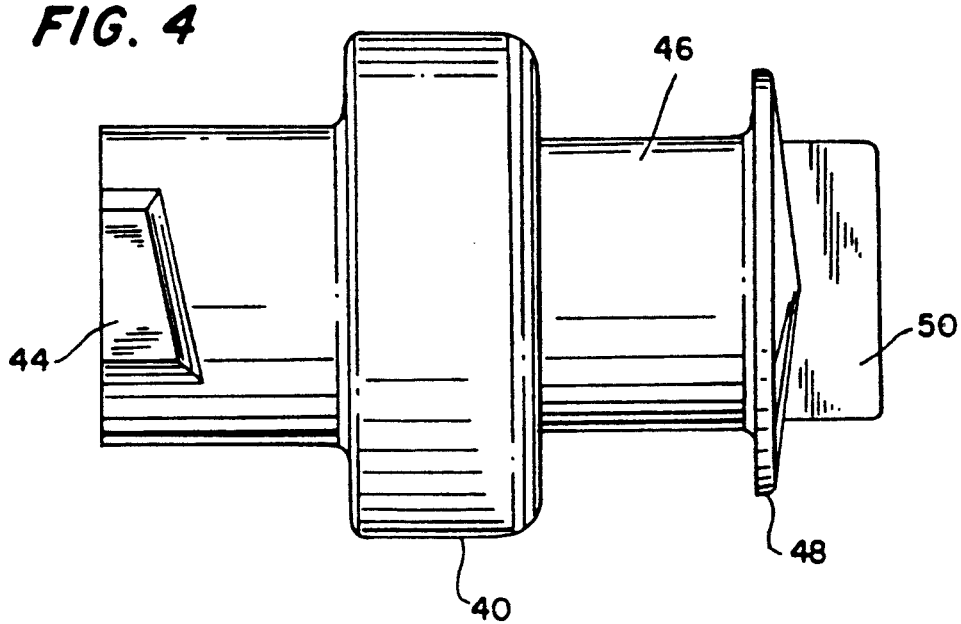
FIG. 4 is a side elevation of the cap alone.

Inside the shield, two protruding ramps 58 (FIGS. 2-3) are formed on the plate surface, astride the axis. Each ramp has a leading edge parallel to the axis (that is, perpendicular to the plate surface), and a trailing edge forming an acute angle with the plate surface. This angle should be less than the angle of repose between the materials of the shield and cap, respectively. An angle of about 30° is now preferred. The protrusions are spaced apart sufficiently, so that the cap blade 50 just spans them.

Three equally spaced semi-circular openings 60 extend through the plate. The flat edge of each opening is just outside the inside diameter of the shell 54. Each of the openings is formed during manufacture, as corresponding core pins, used to form the frangible tangs 62, are withdrawn. Each of the core pins (not shown) has a semi-cylindrical distal portion beveled at an angles corresponding to that of the tangs; the forward tip surface is provided with a recess, which forms the tang integrally with the shell 54.

Each tang 62 protrudes toward the axis of the shell, but obliquely, so that each tang, if extended, would meet the surface of the plate near its center. Tangs having a rectangular cross-section measuring 0.031 inch in the tangential direction by 0.018 have been found to perform well. The preferred inclination is 45° from the axial direction, to ensure complete breakage.

As shown in FIG. 1, a slot 64 may be formed in the shield plate; the slot has lateral dimensions at least equal to those of the cap blade, whereby, once the shield has been removed, it can be used as a screwdriver for unscrewing the cap.

Each of the components of this invention is preferably formed by injection molding from thermoplastic material. The presently preferred material for the cap is polypropylene, because of its chemical compatibility and acceptability for pharmaceutical use. The shield material, on the other hand, is selected more for its mechanical characteristics, especially for its ability to produce reliable tang breakage, yet have good strength and moldability. An acrylic plastic is presently preferred, although a high-impact polystyrene is considered as an alternative.

In use, the cap and shield will normally have been pre-assembled by pushing them together until the tangs hook behind the peripheral flange of the cap. A pharmacist, having filled the syringe with a medication or other fluid, then threads the cap onto the end of the syringe, to seal off the outlet port, and prevent fluid loss and contamination, by turning the shield clockwise while the one-way drive members are engaged. Now, because the shield completely encloses the cap, the cap cannot be unscrewed directly; nor can it be turned by rotating the shield, because of the one-way driving connection between the shield and the cap. The only way the cap can be removed, to get at the contents of the syringe, it to remove the shield forcibly by pulling it off the cap. The tangs are unavoidably broken by such removal, and the fact that the shield no longer is retained on the cap, once the tangs are broken, makes tampering evident. Noticeability is improved if the cap and shield have greatly different coloration. Furthermore, we have found it advantageous to choose a transparent material for the shield, to facilitate inspection of the underlying cap.

Figure 6:
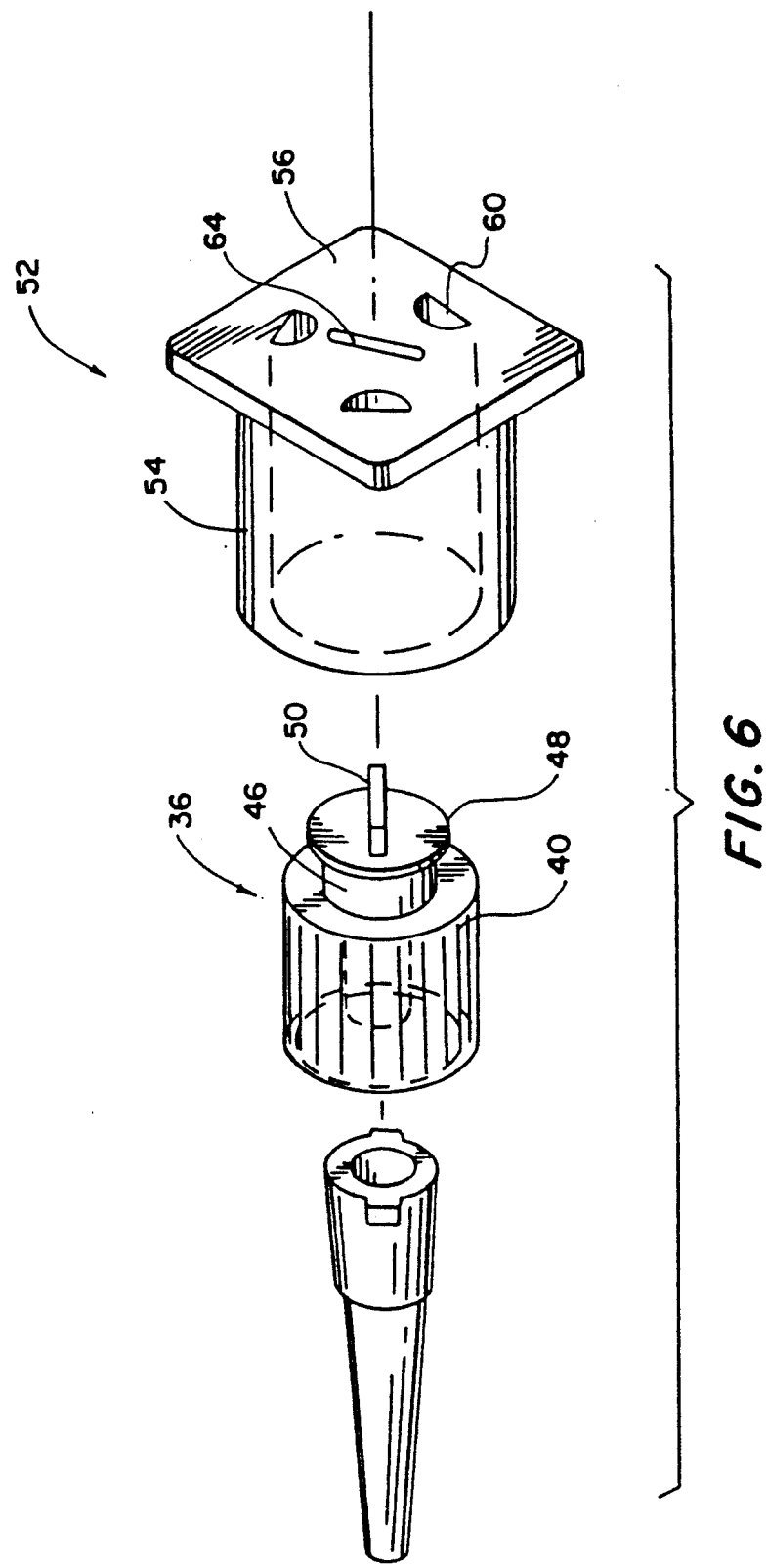
FIG. 6 is an exploded view corresponding to FIG. 1, showing an alternative form of the invention.

The foregoing is a description of the best mode of practicing the invention now contemplated by the inventor. Some variations are presently contemplated as well. For example, one could reverse male and female luer locks, as shown in FIG. 6. This variation is useful where the injection device is not a syringe, but rather an injection port in a fluid infusion line, for example.

Since the invention is subject to other modifications and variations, it is intended that the foregoing description and the accompanying drawings shall be interpreted as illustrative of only one form of the invention. Such variations not presently contemplated may be suggested by this invention and within the scope of the following claims.

I claim:

1. A tamper-resistant closure for a medical injection device having a protruding outlet and a first threaded connector, said closure comprising
    a cap having both a blind bore sized to receive and seat tightly against said outlet, to prevent material from entering or being withdrawn from the injection device, and a threaded portion for mating with said first threaded connector, so that the cap can be screwed onto the injection device by turning the cap in a predetermined direction relative to the injection device, and
    a shield entirely enveloping the cap, and having a loose fit thereon that cannot unscrew the cap, so that the cap cannot be removed from the injection device while the shield is in place, said shield having an internal surface and at least one internal, frangible tang protruding therefrom diagonally toward the cap and diagonally away from the injection device, so that the shield can be pressed onto the cap once the cap has been installed on the injection device, but cannot thereafter be pulled off without breaking the tang and thus providing an indication of tampering, said cap further having a protrusion for engaging said tang.

2. The invention of claim 1, wherein said cap has a proximal end provided with said threads, and a distal end provided with said protrusion.

3. The invention of claim 2, wherein said cap has a reduced diameter portion, and said protrusion is a peripheral flange having a diameter greater than the reduced diameter portion, thus providing a shoulder engaged by said tang.

4. The invention of claim 2, wherein the shield has a plate at its distal end, covering the distal end of said cap, to prevent access to the cap.

5. The invention of claim 4, wherein said plate has an inner surface, within a tubular portion of the shield, and means for turning the cap in only said predetermined direction, so that the cap cannot be removed from the injection device by turning the shield.

6. The invention of claim 5, wherein the shield comprises at least three such tangs, circumferentially spaced around the interior of the shield.

7. The invention of claim 5, wherein said cap further comprises means for engagement with said turning means.

8. The invention of claim 7, wherein said engagement means is a blade protruding in an axial plane from the distal end of the cap, and the turning means is a ratcheting structure on the plate.

9. The invention of claim 8, wherein the shield has a slot formed in its plate, said slot having lateral dimensions at least equal to those of the blade on the cap, whereby, once the shield has been removed, it can be used as a screwdriver for unscrewing the cap from the injection device.

10. The invention of claim 8, wherein the shield has longitudinal axis and the ratcheting structure comprises a pair of spaced ramps protruding from the inner surface of the plate toward the cap, astride the axis of the shield, the ramps each having a surface perpendicular to the inner surface, for driving the blade in said predetermined direction, and an opposite, inclined surface at an angle to the inner surface, said angle being sufficiently acute to prevent the inclined surface from driving the blade in a direction opposite to the predetermined direction.

11. The invention of claim 10, wherein said angle is less than the angle of repose between the materials of the blade and the ramps.

12. The invention of claim 1, wherein the shield has a longitudinal axis, and said tang extends in a direction angled about 45° with respect said axis.

13. The invention of claim 12, wherein said tang has a cross-section measuring about 0.018 inch by 0.031 inch.

* * * * *